(12) United States Patent
Bedingham et al.

(10) Patent No.: US 11,369,336 B2
(45) Date of Patent: Jun. 28, 2022

(54) ERGONOMIC CHESTPIECE

(71) Applicant: 3M Innovative Properties Company, Saint Paul, MN (US)

(72) Inventors: William Bedingham, Woodbury, MN (US); Daniel J. Rogers, Grant, MN (US); Tyler J. Sandback, Prior Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 245 days.

(21) Appl. No.: 16/647,877

(22) PCT Filed: Aug. 15, 2018

(86) PCT No.: PCT/IB2018/056130
§ 371 (c)(1),
(2) Date: Mar. 17, 2020

(87) PCT Pub. No.: WO2019/058191
PCT Pub. Date: Mar. 28, 2019

(65) Prior Publication Data
US 2020/0214660 A1 Jul. 9, 2020

Related U.S. Application Data

(60) Provisional application No. 62/560,470, filed on Sep. 19, 2017.

(51) Int. Cl.
*A61B 7/02* (2006.01)
(52) U.S. Cl.
CPC ....................................... *A61B 7/02* (2013.01)
(58) Field of Classification Search
CPC ....................................................... A61B 7/02
(Continued)

(56) References Cited

U.S. PATENT DOCUMENTS

| 2,513,827 | A |   | 7/1950 | Tynan |  |
|---|---|---|---|---|---|
| 3,339,667 | A | * | 9/1967 | Speelman | A61B 5/02233 181/137 |

(Continued)

FOREIGN PATENT DOCUMENTS

| BR | 9006529 | 8/1992 |
|---|---|---|
| CA | 2061491 | 8/1992 |

(Continued)

OTHER PUBLICATIONS

"3M™ Littmann® Select Stethoscope", Package insert for 3M™ Littmann® Select Stethoscope [retrieved from the internet on Oct. 15, 2018], URL <https://web.archive.org/web/20150830020432/https://multimedia.3m.com/mws/media/362296O/package-insert-for-3m-littmann-select-stethoscope.pdf>, 2018, pp. 1-6.

(Continued)

*Primary Examiner* — Jeremy A Luks (57) ABSTRACT

Aspects of the present disclosure relate to an ergonomic chestpiece for a stethoscope. The chestpiece includes a bottom surface which is generally planar and adapted to be placed near the patient for receiving auscultatory sounds. The chestpiece includes a raised center portion defining first and second lateral indented gripping surfaces, the raised center portion having a top surface opposite the bottom surface. The chestpiece includes a stem portion extending distally from the raised center portion. The first lateral indented gripping surface is defined by a first wall comprising a first concave surface arcuate about a first axis and the second lateral indented gripping surface is defined by a second wall comprising a second concave surface arcuate about a second axis. The first axis and the second axis form a V-shape comprising an apex oriented in a direction of the stem portion.

19 Claims, 9 Drawing Sheets

(58) Field of Classification Search
USPC .......................................... 181/131; D24/134
See application file for complete search history.

(56) References Cited

U.S. PATENT DOCUMENTS

| | | | |
|---|---|---|---|
| D256,951 S | 9/1980 | Allen | |
| 4,440,258 A | 4/1984 | Packard | |
| D277,890 S | 3/1985 | Loughridge | |
| 4,823,906 A | 4/1989 | Gabriel | |
| D323,394 S | 1/1992 | Casto | |
| 5,111,904 A | 5/1992 | Packard | |
| 5,204,500 A | 4/1993 | Dufresne | |
| D337,381 S | 7/1993 | Dufresne | |
| D338,269 S | 8/1993 | Dufresne | |
| 5,380,182 A | 1/1995 | Packard | |
| 5,466,897 A * | 11/1995 | Ross | A61B 7/02 181/131 |
| D373,824 S | 9/1996 | Packard | |
| D379,512 S | 5/1997 | Dieken | |
| 5,663,532 A | 9/1997 | Dieken | |
| 5,747,752 A * | 5/1998 | Selinger | A61B 7/02 181/131 |
| D395,509 S * | 6/1998 | Packard | D24/137 |
| 5,796,053 A | 8/1998 | Shieh | |
| D403,065 S | 12/1998 | Dieken | |
| D410,285 S | 5/1999 | Packard | |
| D432,238 S * | 10/2000 | Packard | D24/134 |
| 6,340,350 B1 | 1/2002 | Simms | |
| 6,520,281 B1 * | 2/2003 | Deslauriers | A61B 7/02 181/131 |
| 6,966,400 B1 | 11/2005 | Rollins | |
| 7,516,814 B1 | 4/2009 | Berk | |
| D750,241 S | 2/2016 | Shan | |
| D837,979 S * | 1/2019 | Shan | D24/134 |
| D847,986 S * | 5/2019 | Shan | D24/134 |
| D858,759 S | 9/2019 | Bedingham | |
| 2003/0002685 A1 | 1/2003 | Werblud | |
| 2003/0047376 A1* | 3/2003 | Oster | A61B 7/02 181/131 |
| 2003/0201138 A1* | 10/2003 | Drummond | A61B 7/02 181/131 |
| 2006/0098825 A1* | 5/2006 | Katz | A61B 7/04 381/67 |
| 2007/0113649 A1 | 5/2007 | Bharti | |
| 2007/0113654 A1 | 5/2007 | Carim | |
| 2008/0137876 A1 | 6/2008 | Kassal | |
| 2008/0232604 A1 | 9/2008 | Dufresne | |
| 2008/0232605 A1 | 9/2008 | Bagha | |
| 2009/0212234 A1 | 8/2009 | Vestal | |
| 2010/0155173 A1 | 6/2010 | Boyd | |
| 2011/0048841 A1* | 3/2011 | Hasbun | A61B 7/02 181/131 |
| 2014/0254814 A1 | 9/2014 | Van Alstine | |
| 2016/0287207 A1 | 10/2016 | Xue | |

FOREIGN PATENT DOCUMENTS

| | | |
|---|---|---|
| CN | 3510339 | 3/2006 |
| CN | 3584903 | 11/2006 |
| CN | 300901549 | 4/2009 |
| CN | 201409930 | 2/2010 |
| CN | 301162863 | 3/2010 |
| CN | 301247780 | 6/2010 |
| CN | 201759580 | 3/2011 |
| CN | 301796333 | 1/2012 |
| CN | 301942067 | 5/2012 |
| CN | 302945032 | 9/2014 |
| CN | 204192651 | 3/2015 |
| CN | 105581810 | 5/2016 |
| CN | 304062471 | 3/2017 |
| CN | 304119155 | 4/2017 |
| DE | 4029122 | 3/1992 |
| DE | M9105644-0001 | 3/1992 |
| DE | M9105644-0002 | 3/1992 |
| DE | M9105644-0003 | 3/1992 |
| DE | M9500776-0001 | 7/1995 |
| DE | M9500776-0002 | 7/1995 |
| DE | 20306950 | 7/2003 |
| DE | 10320011 | 12/2004 |
| EM | 002518068-0001 | 8/2014 |
| EM | 002953497-0001 | 1/2016 |
| EM | 003790393-0001 | 3/2017 |
| EM | 003790393-0002 | 6/2017 |
| EP | 2945084 | 11/2015 |
| FR | 2722677 | 1/1996 |
| GB | 729277 | 5/1955 |
| JP | 2012055354 | 3/2012 |
| RU | 122867 | 12/2012 |
| WO | WO D019101-002 | 3/1991 |
| WO | WO D019101-003 | 3/1991 |
| WO | WO D019101-004 | 3/1991 |
| WO | WO D019101-007 | 3/1991 |
| WO | WO D019101-008 | 3/1991 |
| WO | WO 1997-019639 | 6/1997 |
| WO | WO 1997-019640 | 6/1997 |
| WO | WO 1998-034530 | 8/1998 |
| WO | WO 1998-051221 | 11/1998 |
| WO | WO 2006-071948 | 7/2006 |
| WO | WO 2006-136734 | 12/2006 |
| WO | WO 2007-047929 | 4/2007 |
| WO | WO 2007-106804 | 9/2007 |
| WO | WO 2013-156999 | 10/2013 |
| WO | WO 2014-167155 | 10/2014 |
| WO | WO 2014-204518 | 12/2014 |
| WO | WO 2015-040610 | 3/2015 |
| WO | WO 2015-105730 | 7/2015 |

OTHER PUBLICATIONS

International Search Report for PCT International Application No. PCT/IB2018/056130, dated Nov. 14, 2018, 3 pages.

* cited by examiner

ERGONOMIC CHESTPIECE

CROSS REFERENCE TO RELATED APPLICATIONS

This application is a national stage filing under 35 U.S.C. 371 of PCT/IB2018/056130, filed Aug. 15, 2018, which claims the benefit of U.S. Provisional Application No. 62/560,470, filed Sep. 19, 2017, the disclosures of which are incorporated by reference in their entirety herein.

BACKGROUND

Stethoscopes have long been used by physicians to monitor auscultatory sounds. Typically, stethoscopes have been comprised of a head or chestpiece, a sound transmission mechanism and a headset assembly. The chestpiece is adapted to be placed against the skin of a patient for gathering auscultatory sounds. The sound transmission mechanism transmits the gathered sound to the earpiece of the headset assembly where the physician may monitor the sound.

Traditionally, stethoscopes have been designed primarily to optimize acoustic performance for the user and, secondarily, to provide an attractive design/color for personal use. Double-sided stethoscopes have a large acoustic sensor element on both the top and bottom surface of the "chestpiece" and forces the user to grip the chestpiece around these elements. Single-sided stethoscopes have a single acoustic element on the bottom surface and a top surface for the user to hold the chestpiece.

SUMMARY

Single-sided stethoscopes can often look "aesthetically pleasing" and have "apparent" grip features, but they may be suboptimal for holding the chestpiece, do not conform to the human hand anatomy, provide only limited grip positions, and do not necessarily allow the user to transition seamlessly between grip positions.

Aspects of the present disclosure relate to an ergonomic chestpiece for a stethoscope. The chestpiece includes a bottom surface which is generally planar and adapted to be placed near the patient for receiving auscultatory sounds. The chestpiece includes a raised center portion defining first and second lateral indented gripping surfaces, the raised center portion having a top surface opposite the bottom surface. The chestpiece includes a stem portion extending distally from the raised center portion. The first lateral indented gripping surface is defined by a first wall comprising a first concave surface arcuate about a first axis and the second lateral indented gripping surface is defined by a second wall comprising a second concave surface arcuate about a second axis. The first axis and the second axis form a V-shape comprising an apex oriented in a direction of the stem portion.

DETAILED DESCRIPTION

Aspects of the present disclosure relate to a chestpiece having one or more ergonomic features. The ergonomic features are configured to fit the way that a human hand grips objects and can allow a user to comfortably grip and transition between different handholds. The user does not actively grip the device, and can relax the hand muscles which can provide an intuitive "feel," reduce fatigue, and potential noise from muscle twitch, movement, or tremor from the user. The stethoscope 10 illustrated in FIG. 1 includes a chestpiece 13, or stethoscope head, a headset 14 and a connecting tubing 16. The headset 14 has two eartips 18 and 20, adapted to fit in the ear of a user, typically a physician or other medical professional. Tubing 22 and 24, generally acoustic tubing, couple eartips 18 and 20, respectively to connecting tubing 16, which in turn is coupled to chestpiece 13.

Figure 1:
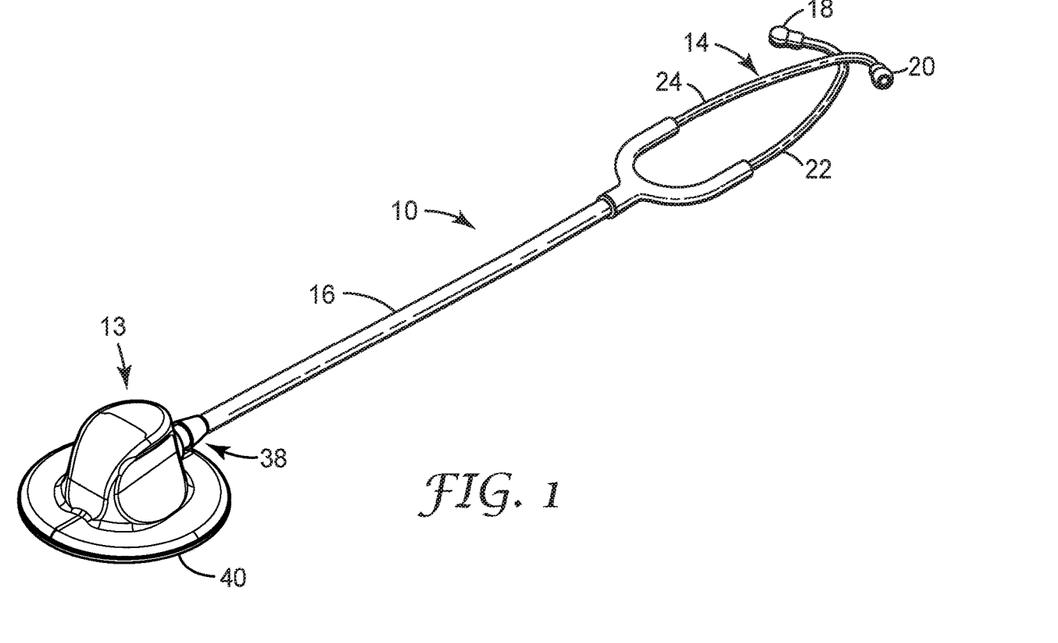
FIG. 1 is a top plan view illustrating a stethoscope incorporating the chestpiece according to one embodiment of the present disclosure.

The sound transmission system of stethoscope 10 may be acoustic as is known in the art. However, it is also contemplated that the sound transmission system of stethoscope 10 could also be electronic. The chestpiece 13 can couple to the connecting tubing 16 via a stem portion 38 that inserts into an opening formed in the connecting tubing 16. The connecting tubing 16 can surround the stem portion 38 and form a secure connection. In at least one embodiment, the stem portion 38 can be releasably attached from the connecting tubing 16.

The chestpiece 13 can also have a diaphragm 40 removably attached. The diaphragm 40 can be diaphragms such as those commercially available under the trade designation Littmann from 3M (St. Paul, Minn.). The diaphragm can transmit auscultatory vibrations from the skin of a patient and, optionally, through a layer of clothing.

A kit may be formed that includes any component of the stethoscope 10. For example, the chestpiece 13, diaphragm 40, a headset 14, a connecting tubing 16, or combinations thereof can be included in the kit. The kit can also include the stethoscope 10 and any corresponding packaging for the stethoscope 10.

FIGS. 2A-2G illustrate an embodiment of a chestpiece 13 shown in FIG. 1. The chestpiece 13 can generally be adapted to fit an adult patient.

Figure 2A:
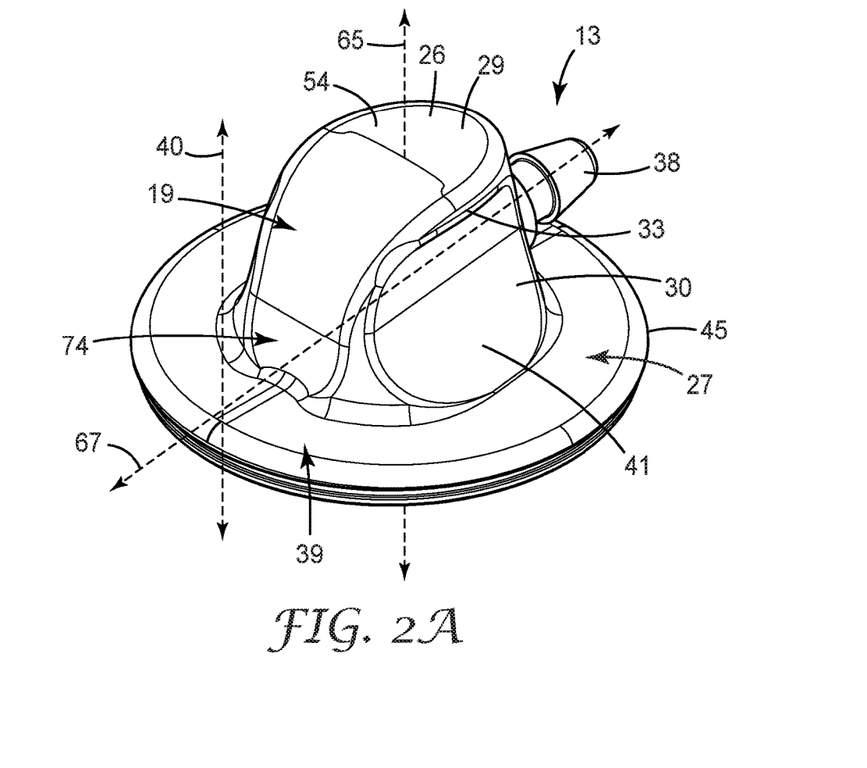
FIG. 2A is a perspective view of an illustrative embodiment of the chestpiece, according to various aspects of the present disclosure.

In FIG. 2A, the (ergonomic) chestpiece 13 can be adapted to be placed near the source of auscultatory sound, or, in a preferred embodiment, to contact the skin of the patient. For example, the chestpiece 13 can have a bottom surface 41 (discussed further herein) that can be adapted to be proximate the skin of a patient.

The chestpiece 13 can have a bottom surface 41 that is an elliptical shape. As used herein, the term elliptical shape can refer to a shape having elliptical properties. For example, an elliptical shape can refer to an ellipse, an elliptical prism, a circle, a sphere, or a cylinder. An elliptical prism can comprise one or more ellipses. In at least one embodiment, the bottom surface 41 is circular. The bottom surface 41 is configured to contact a diaphragm (which can contact the skin of the patient). In some embodiments, the bottom surface 41 is configured to secure a removable diaphragm.

Figure 2B:
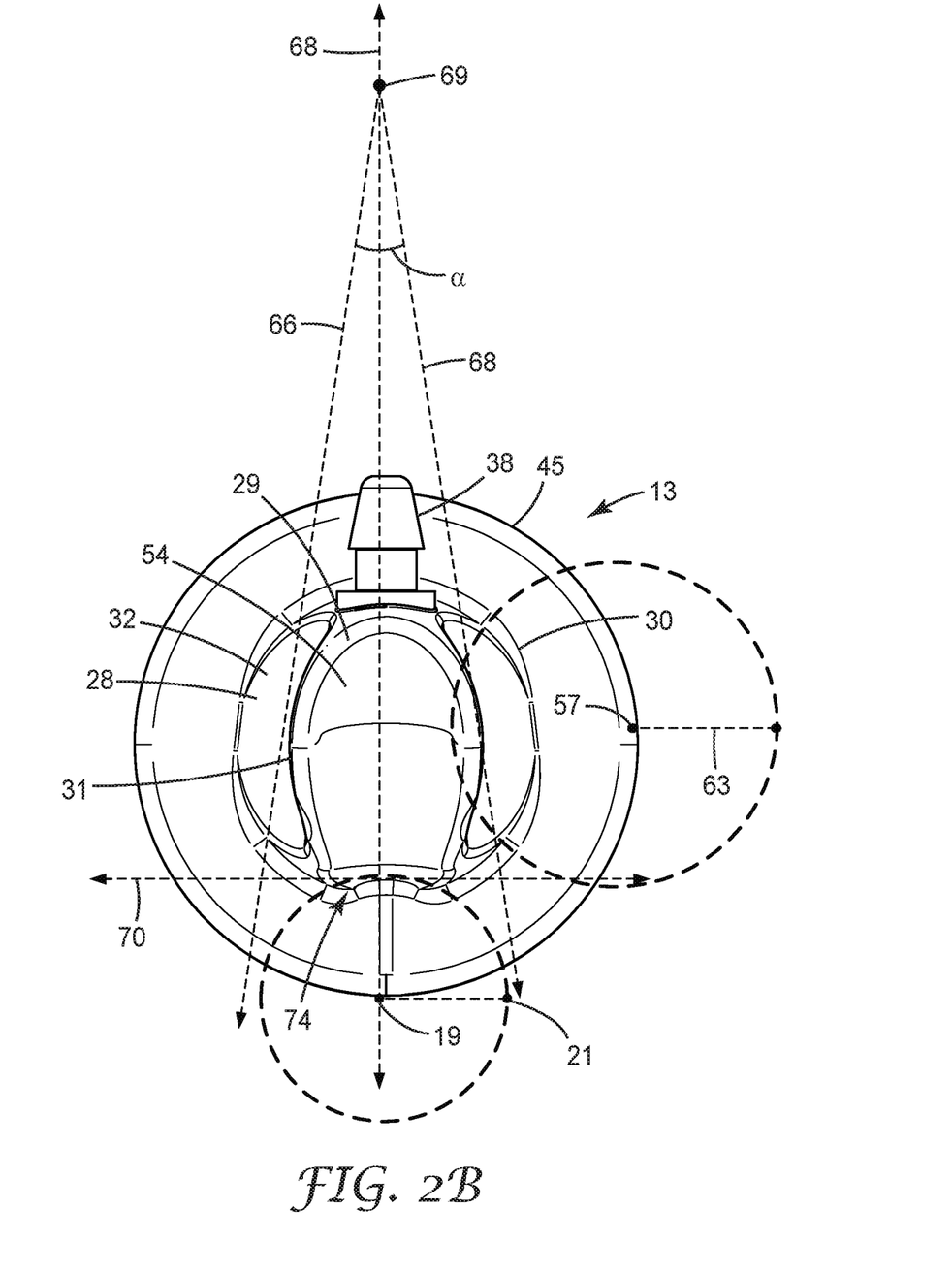
FIG. 2B is a top view of the chestpiece of FIG. 2A, according to various aspects of the present disclosure.
Figure 2C:
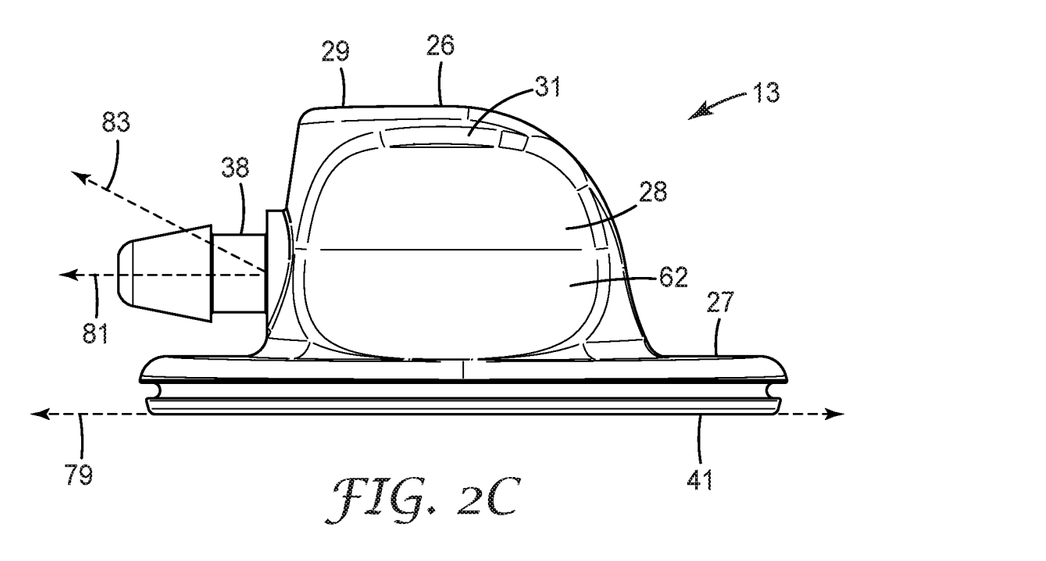
FIG. 2C is a side view of the chestpiece of FIGS. 2A-2B, according to various aspects of the present disclosure.
Figure 2D:
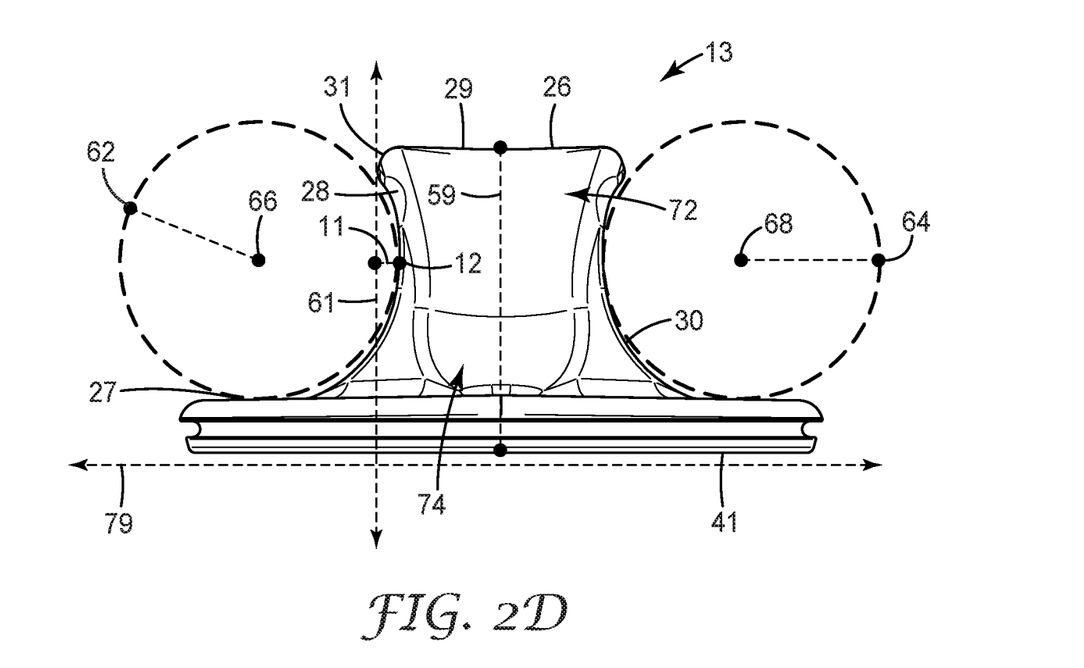
FIG. 2D is a front view of the chestpiece of FIGS. 2A-2C, according to various aspects of the present disclosure.
Figure 2E:
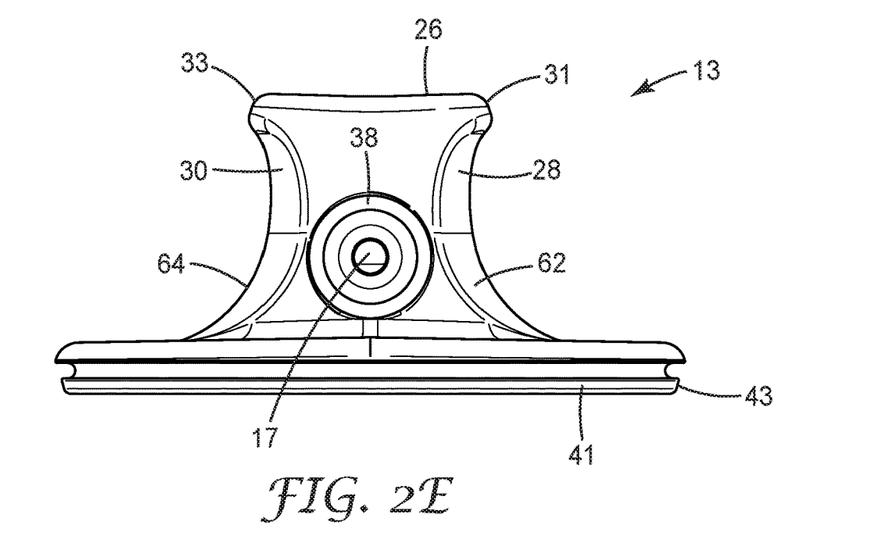
FIG. 2E is a rear view of the chestpiece of FIGS. 2A-2D, according to various aspects of the present disclosure.
Figure 2F:
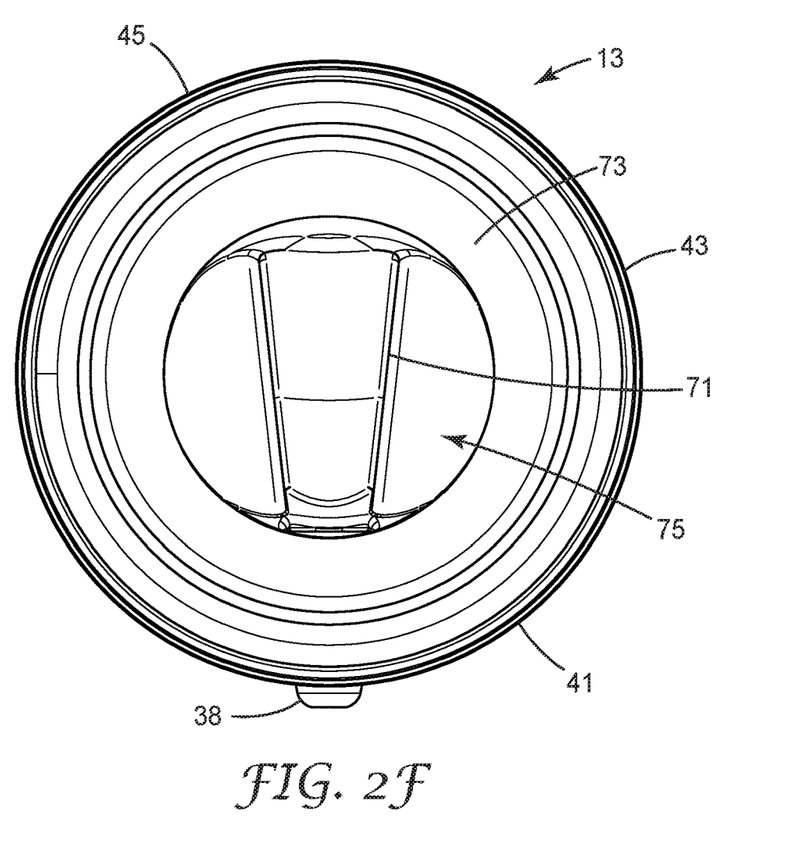
FIG. 2F is a bottom view of the chestpiece of FIGS. 2A-2E, according to various aspects of the present disclosure.
Figure 4A:
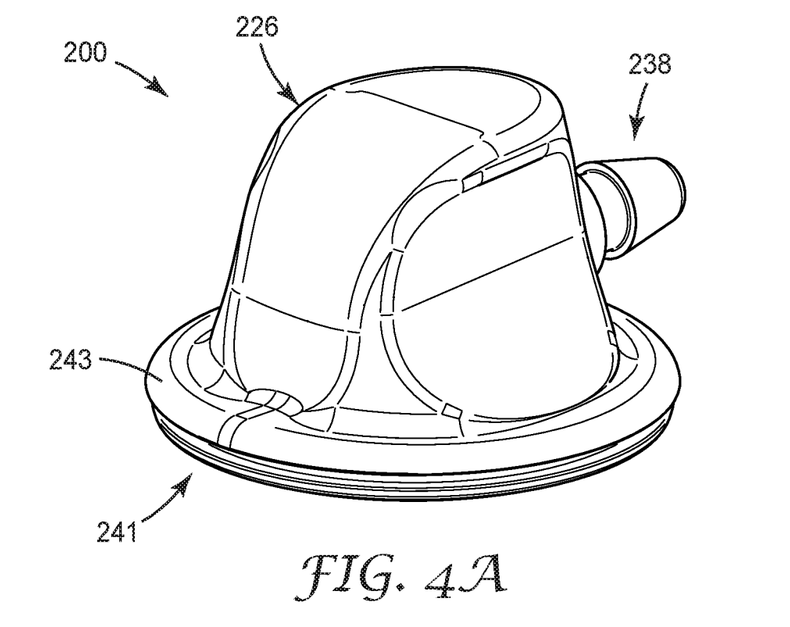
FIG. 4A is a perspective view of an illustrative embodiment of the chestpiece, according to various aspects of the present disclosure.

The chestpiece 13 can further can have an outer perimeter 45 which is also shown in other figures herein (e.g., FIG. 2F). The outer perimeter 45 is an edge of the chestpiece 13 and may be different than the bottom surface 41. In at least one embodiment, the outer perimeter 45 is established from a lower portion 39 of the chestpiece 13 and is generally established within the same plane. In at least one embodiment, the outer perimeter 45 can be an oval. The outer perimeter 45 can also be of various dimensions relative to a raised center portion 26 (described herein). For example, the outer perimeter 45 can be at least 1.5 times the diameter of the raised center portion 26. In another example, (e.g., a pediatric embodiment described in FIG. 4) the outer perimeter 45 is less than 1.5 times the diameter of the raised center portion 26.

Turning to FIG. 2F, the bottom surface 41 can be generally planar. As used herein, the term "generally" or "about" can mean plus or minus 5% variance. For example, a generally planar (i.e., 180 degrees) bottom surface 41 can mean plus or minus 9 degrees. The bottom surface 41 can be adapted to mate with a diaphragm (e.g., 40 in FIG. 1) which contacts the patient. The bottom surface 41 can include a rim portion 43 that is configured to mate with or removably secure the diaphragm. As shown, the rim portion 43 can include a lip that is configured to removably secure the diaphragm (such as 40 in FIG. 1). The rim portion 43 can form a diaphragm opening that can lead into the bell cavity 75 of the chestpiece 13. The bell cavity 75 can be formed from the diaphragm opening formed from the rim portion 43, the interior 73 of a lower portion 39 (shown in FIG. 2A), and the interior 71 of a raised center portion 73 (described herein).

Turning to FIG. 2A, the lower portion 39 of the bell has an upper surface 27. The upper surface 27 is opposite from the bottom surface 41 and a portion of the upper surface 27 can form bell cavity 75 (as shown in FIG. 2F) with a portion of the bell (e.g., an upper surface).

The chestpiece 13 can be oriented along axes 65 and 67. In at least one embodiment, axis 67 can be the median axis and axis 65 can be a z-axis or a vertical axis. The raised center portion 26 can extend distally in the direction of axis 65 and the stem portion 38 can extend distally in the direction of axis 67.

The chestpiece 13 can have a raised center portion 26 which can have the ergonomic features discussed herein. The raised center portion 26 has an indented gripping surface. In at least one embodiment, the raised center portion 26 has at least two indented gripping surfaces or even at least three indented gripping surfaces. The indented gripping surfaces of the raised center portion 26 are adapted to easily, securely and comfortably engage the gripping appendages (as shown herein) of the user.

In FIG. 2D, indented gripping surfaces 28 and 30 are shown. Indented gripping surfaces 28 and 30 can be defined as lateral indented gripping surfaces. Indented gripping surfaces 28 and 30 are defined by walls which are arcuate about one or more axes. The one or more axes can be orthogonal or parallel to the bottom surface of chestpiece 13. In at least one embodiment, the indented gripping surfaces 28 and 30 are arcuate about an axis generally parallel to the bottom surface of the chestpiece 13 to create an indented impression in the indented gripping surfaces 28 and 30 into which the thumb and/or fingers of the user can securely and comfortably fit.

For example, the indented gripping surface 30 can be defined by a wall comprising a second concave surface arcuate about axis 68. In at least one embodiment, the axis 68 is generally parallel to the bottom surface 41 (which may be defined by the plane 79). In at least one embodiment, the axis 68 can form an angle of no greater than 15 degrees with respect to the bottom surface 41 (e.g., plane 79) or, in other embodiments, relative to axis 66. The indented gripping surface 30 can have a radius of curvature defined by 64. In at least one embodiment, the radius of curvature 64 is at least 6 mm, at least 7 mm, at least 8 mm, at least 9 mm, at least 10 mm, or even at least 11 mm. In at least one embodiment, the radius of curvature 64 can be no greater than 20 mm, no greater than 18 mm, or no greater than 15 mm.

In at least one embodiment, at least one of the indented gripping surfaces 28 and 30 can be arcuate about a elliptical shape such as a circle or an ellipse. The elliptical shape shown is primary circular but elliptical embodiments are contemplated. For example, an elliptical prism can be oriented along axis 68 (meaning that the height dimension of the elliptical prism is oriented along the axis 68). The indented gripping surface 30 can be arcuate about the elliptical prism (i.e., a notional surface of the elliptical prism) or one or more ellipses defining the elliptical prism.

Similarly, the indented gripping surface 28 can be defined by a wall comprising a first concave surface arcuate about axis 66. In at least one embodiment, the indented gripping surface 28 can have a radius of curvature 62 having similar or the same dimensions of radius of curvature 64 described herein. In at least one embodiment, the indented gripping surface 28 can have a radius of curvature 62 that is different than radius of curvature 64. For example, the radius of curvature 62 can be 10 mm while radius of curvature 64 is 9 mm to accommodate finger holds between the middle and index fingers of the user.

Figure 4B:
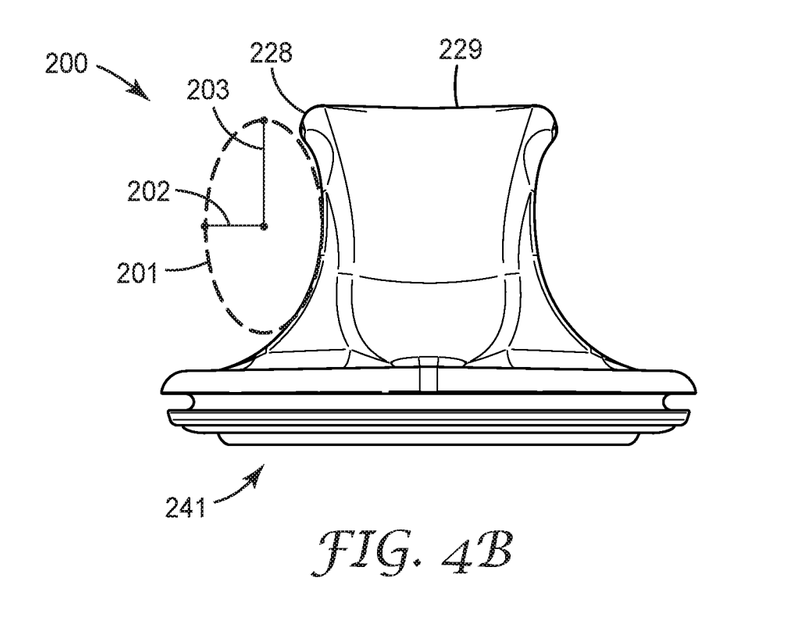
FIG. 4B is a front view of an illustrative embodiment of the chestpiece of FIG. 4A, according to various aspects of the present disclosure.
Figure 4C:
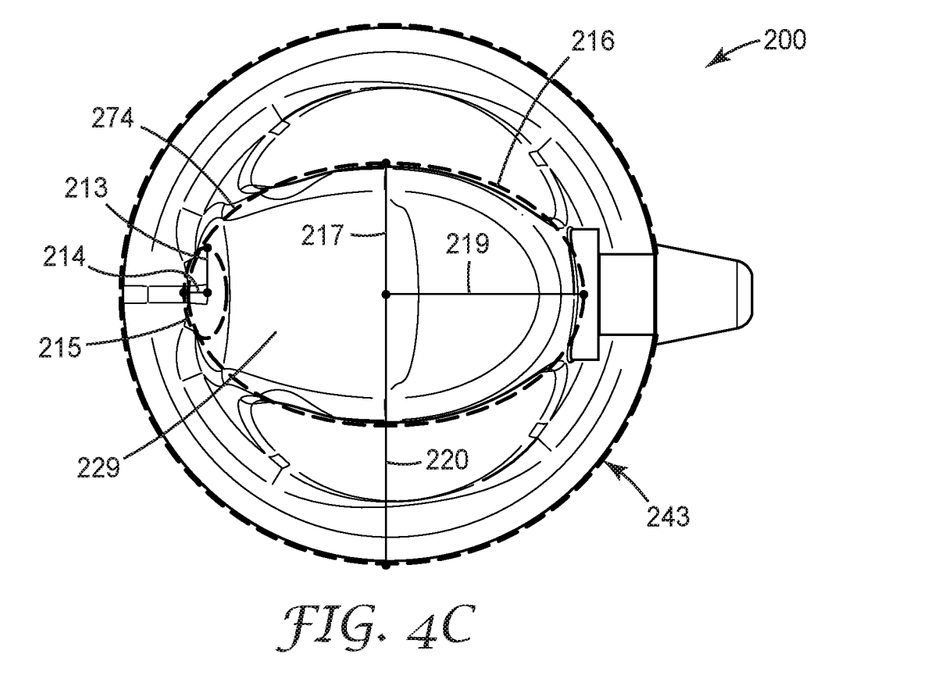
FIG. 4C is atop elevational view of an illustrative embodiment of the chestpiece of FIGS. 4A-4B, according to various aspects of the present disclosure.

Although depicted as having a circular radius of curvature, the dimensions of the lateral indented gripping surfaces 28 and 30 and/or the front indented gripping surface can also be arcuate about an elliptical shape (similar to that of the embodiment in FIGS. 4A-4C).

In at least one embodiment, the indented gripping surfaces 28 and 30 can have a concave surface that is continuous along an entire wall.

In at least one embodiment, the indented gripping surfaces 28 and 30 form a recess defined by a top surface 29 therein opposite the bottom surface 41. The top surface 29 is the topmost surface of the raised center portion 26. The top surface 29 differs from the upper surface 27 in that the top surface 29 can have a greater height relative to the bottom surface 41.

The top surface 29 can have a protruding edge 31 and 33 (shown in FIGS. 2A, 2E) formed therein. The protruding edges 31 and 33 can overhang off the intended gripping surfaces 28, and 30. The area formed by the indented impressions in the walls of indented gripping surfaces 28 and 30, and their respective protruding edges 31 and 33 can define lateral recesses which are adapted to receive at least one finger of the user.

In at least one embodiment, the indented impressions of the lateral recesses formed into raised center portion 26 allow indented gripping surfaces 28 and 30 and the associated protruding edges 31 and 33 to allow comfortable placement and secure gripping of the chestpiece by the user. The protruding edges 31 and 33 on indented gripping surfaces 28 and 30 prevent the fingers or thumb of the user from slipping upward during use and reduces the possibility that the chestpiece will slip out of the user's grip during use.

In at least one embodiment, the protruding edges 31 and 33 can have a horizontal distance 11. The horizontal distance 11 of protruding edge 31 can be measured between axis 61 that contacts the distal-most point of the top surface 29 and the median-most point 12. The horizontal distance 11 of the protruding edge 31 can be measured relative to the median-most point 12 of the concave surface measured along a plane parallel to a plane 79. In at least one embodiment, the horizontal distance 11 is between 1 and 4 mm (inclusive), even more preferably, the horizontal distance 11 is between 2 and 3 mm (inclusive).

The chestpiece 13 can have a particular height 59. In at least one embodiment, the height 59 can be defined from a portion of the top surface 29 to a portion of the bottom surface 41 (preferably within the same plane). For example, the height 59 can be measured along a median plane (e.g., formed by axis 65 and 67 in FIG. 2A) of the chestpiece 13. While many heights are possible, the preferred height 59 can be from 15 mm to 30 mm (inclusive), 15 mm to 25 mm (inclusive), 20 mm to 25 mm (inclusive), or 20 mm to 22 mm (inclusive).

The indented gripping surfaces 28 and 30 can form a V-shape (when viewed elevationally from the top or bottom). The V-shape can allow for greater comfort of a user when holding between two fingers. The V-shape can follow the contours of the walls forming the gripping surfaces. Turning to FIG. 2B, the V-shape can be defined by axes 66 and 68. For example, axis 66 defines the indented gripping surface 28 while axis 68 defines indented gripping surface 30. The two axes 66 and 68 can meet at an apex 69. The apex 69 can be oriented in the direction of the stem portion 38 (toward the rear of the chestpiece 13). In at least one embodiment, the apex can correspond to the angle between fingers of a user in order to provide an ergonomic grip. In at least one embodiment, the apex has an angle a of between 5 and 35 degrees (inclusive), between 5 and 30 degrees (inclusive) between 5 and 25 degrees (inclusive), between 5 and 20 degrees (inclusive), between 5 and 15 degrees (inclusive), between 10 and 15 degrees (inclusive), or preferably, between 12 and 14 degrees (inclusive).

In at least one embodiment, any portion of the chestpiece 13 can be concavely curved in two directions. In at least one embodiment, a portion of the indented gripping surface 30 or top surface can be concavely curved in two directions; from the front toward the back, and from the top toward the bottom.

The chestpiece 13 is shown as straight along the axes 66 and 68, thus the walls of the indented gripping surface 30 is arcuate along one axis (e.g., axis 68). The chestpiece 13 is shown with a protruding edge 31 being partially defined by an axis 57 that is orthogonal or normal to the bottom surface 41. A portion of the indented gripping surface 28 (such as the edge 31, which is considered part of the top surface 29 and the indented gripping surface 28 for the purpose of this example) can be arcuate to axis 57 (in addition to axis 66). In at least one embodiment, the radius of curvature 63 can be defined based on the outer perimeter 45. For example, the radius of curvature 63 of the indented gripping surface 28 can be at least one-fourth, or one-half of a radius of curvature of the chestpiece outer perimeter 45. In at least one embodiment, the radius of curvature 63 can be based on an dimension. For example, the radius of curvature 63 of the indented gripping surface 30 (or 28) can be at least 5 mm, at least 7 mm, or at least 10 mm.

The raised center portion 26 can also include a indented gripping surface 74 (which may be referred to as a front indented gripping surface 74. The indented gripping surface 74 can defined in part by a front wall 72 (which is also shown on FIG. 2D) comprising a third concave surface arcuate about axis 19. In at least one embodiment, the front wall 72 can extend past the indented gripping surface 74 toward the top surface 29. The axis 19 can be normal to the bottom surface 41. The indented gripping surface 74 can be similar to indented gripping surfaces 28 and 30.

Turning to FIG. 2A, the top surface 29 can further include an indented finger portion having a radius of curvature sufficient for a finger. In at least one embodiment, the radius of curvature is no greater than 10 mm. The front wall 72 can have a radius of curvature no greater than 10 mm. In at least one embodiment, the front wall 72 is an intermediate surface that blends the indented portions from the top surface 29 and the indented gripping surface 74.

Returning to FIG. 2B, in at least one embodiment, the indented gripping surface 74 is defined by axis 70 which is perpendicular to axis 67. The indented gripping surface 74 is adjacent to axis 70. In at least one embodiment, the indented gripping surface 74 intersects axis 70 at least two points. The axis 70, axis 66, and axis 68 can all form a triangle. In at least one embodiment, the triangle is non-equilateral.

The indented gripping surface 74 can further have a radius of curvature 21 similar to the radius of curvatures 62, 64 described in FIG. 2D. In at least one embodiment, the radius of curvature 21 is less than the radius of curvature 63.

In at least one embodiment, any of the indented gripping surfaces (e.g., 28, 30 or 74) can have a roughened texture. The indented gripping surfaces have a regularly scored surface. For example, to further increase the security of the indented gripping surfaces 28, 30 or 74, the walls of the indented gripping surfaces may be roughened, textured, or have ridges formed thereon. The roughened surface may be regular or irregular. In the case of a regularly textured surface, the walls of the indented gripping surfaces 28 30 or 74 may be scored or impressed with a fish gill or knurled pattern, for example. By roughening or texturing the walls of the indented gripping surfaces 28 30 or 74, the security of the chestpiece in the hand is improved. In addition, the ability of the user to adequately grip the chestpiece is improved, thus reducing the likelihood of the chestpiece 13 slipping out of the user's grip and allowing the user to reduce/minimize effort needed to hold device.

Turning to FIG. 2C, a portion of the top surface 29 can be sloped with respect to said bottom surface 41. For example, a portion of the top surface 29 can be closer to the bottom surface 41 at the front (i.e., opposite from the stem portion 38) of the chestpiece 13 than at the rear of the chestpiece 13 (i.e., in the direction of the stem portion 38). In at least one embodiment, the top surface of raised center portion 26 preferably is sloped downward from rear to front of chestpiece 13 to form a surface which may be easily formed into the palm of the hand of the user. Thus, raised center portion 26 is taller at the rear of the chestpiece 13 than at the front of the chestpiece 13. In at least one embodiment, the top surface 29 can include a finger recess 54 (as shown in FIG. 2A). The finger recess 54 can be formed from a portion of the top surface 29.

In at least one embodiment, a finger recess can be located on at least one of the indented gripping surfaces. Finger recesses can provide rest positions for the user's fingers to enhance grip when in alternate positions. Finger recesses can also provide the user with tactile feedback concerning the location of finger hold positions. In at least one embodiment, finger recesses are distinguished from the indented grip portions by the overall width. For example, finger recesses can be dimensioned such that two or more fingers or more than one finger pad of the user will not fit within one finger recess.

Figure 2G:
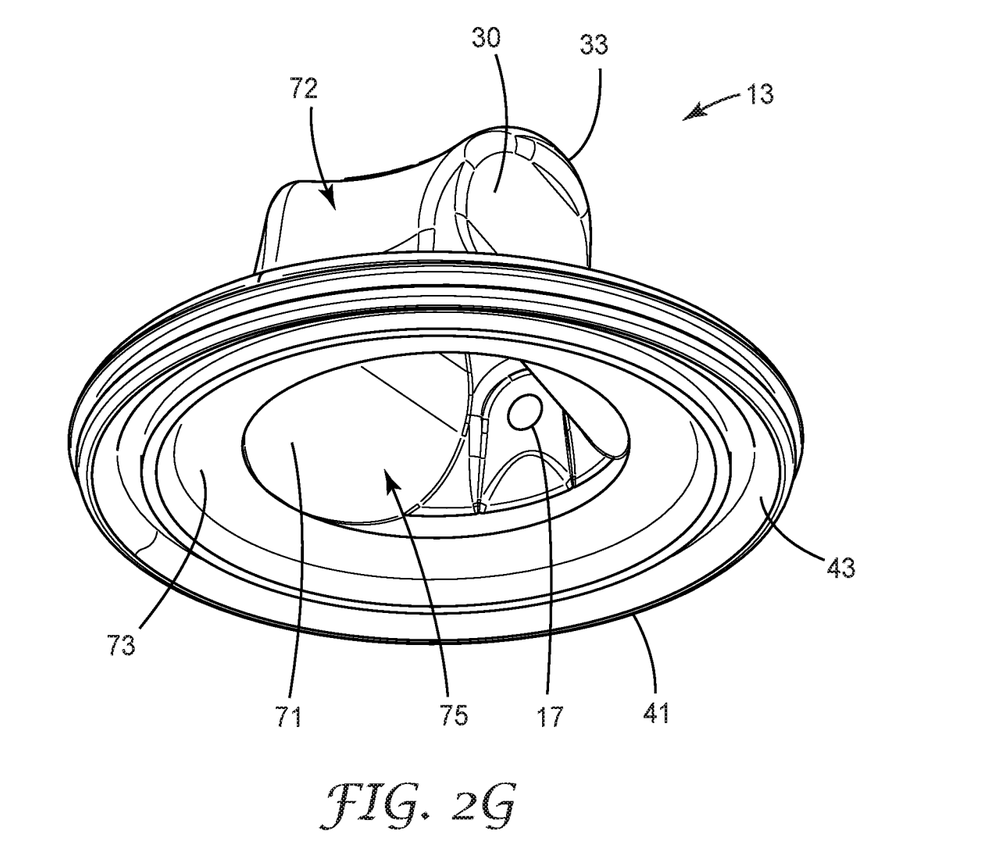
FIG. 2G is a bottom perspective view of the chestpiece of FIGS. 2A-2F, according to various aspects of the present disclosure.

The chestpiece 13 can have a stem portion 38 disposed on a portion of the raised center portion 26. The stem portion 38 can be generally parallel (i.e., plus or minus 9 degrees) to the bottom surface 41 meaning that the stem portion 38 which is aligned with axis 81 which is further parallel to the bottom surface 41 (defined by plane 79). In at least one embodiment, the stem portion 38 can be askew (meaning aligning with axis 83 and forming greater than a 9 degree angle) relative to the bottom surface 41 (defined by plane 79). The stem portion 38 can further include a hole 17 formed therein which opens into the bell cavity 75 such that the stem portion 38 is fluidically coupled to the bell cavity 75 (as shown in FIG. 2E, 2F, and 2G).

In at least one embodiment, the chestpiece 13 can be disposable, meaning that the chestpiece 13 is designed to be disposed of after a single use. The chestpiece 13 can be made from a polymeric material to facilitate disposal. In at least one embodiment, the chestpiece 13 can be made from a metal such as aluminum or steel.

FIGS. 3A-3D illustrate various holding positions of a stethoscope 100. The stethoscope 100 can include the chestpiece 13 of FIGS. 2A-2G. The chestpiece 13 is attached to a tubing 102 which further facilitates the holding positions of a user's hand 101.

Figure 3A:
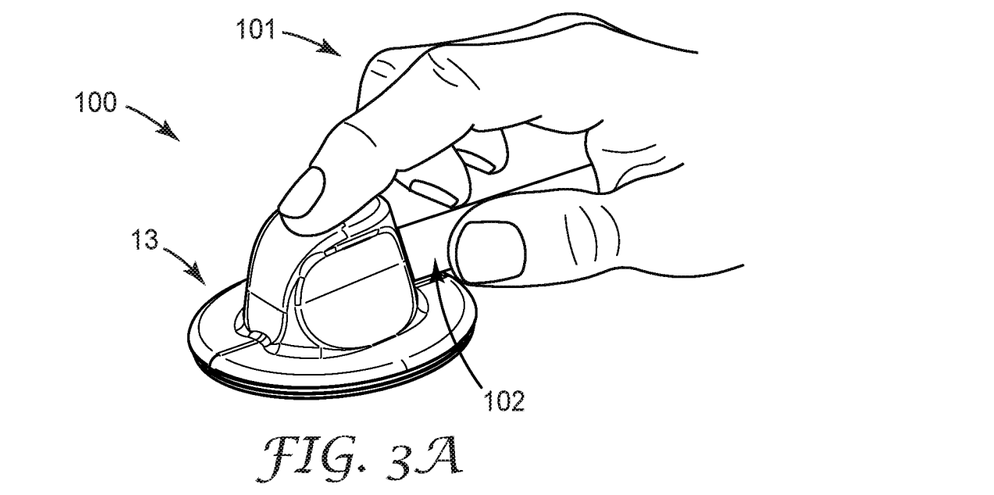
FIGS. 3A-3D illustrate various finger hold positions of the chestpiece of FIGS. 2A-2G, according to various aspects of the present disclosure.

FIG. 3A illustrates where an index finger of a hand 101 applies downward force in the direction of a patient at the finger recess on the top surface. The finger recess further secures the finger from lateral movements. The thumb and middle fingers can further secure the tubing 102 to stabilize the chestpiece 13.

Figure 3B:
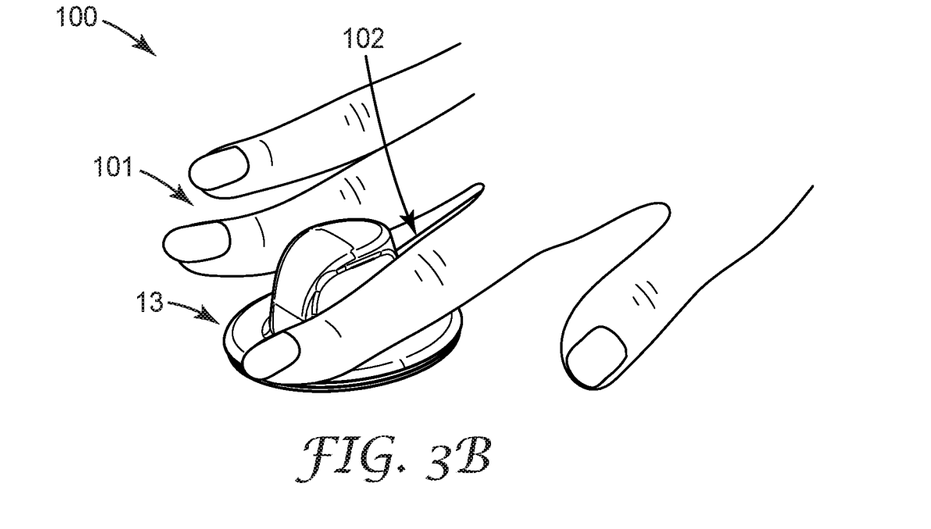

FIG. 3B illustrates where the lateral portions of two adjacent fingers (e.g., an index finger and middle finger) of a hand 101 apply pressure on the raised center portion and maintain an ergonomic angle.

For example, chestpiece 13 has a raised center portion which is adapted to be grasped by the fingers of the user. The protruding edges facilitate the physical stop of the user's fingers from slipping upward. In addition, because the lateral indented gripping surfaces are indented inwards (an in a V-shape) to fit the curve of the user's fingers, the user is provided with tactile feedback concerning the positioning of the chestpiece in the hand. This feedback allows the user to know, understand and adjust, if necessary, the positioning of the chestpiece in the hand without having to visually perceive the chestpiece.

The lateral indented gripping surfaces can be further adapted to receive two lateral sides of two fingers of the user. For instance, the lower portion can form a physical stop for the two lateral sides of two fingers from contacting the patient.

Figure 3C:
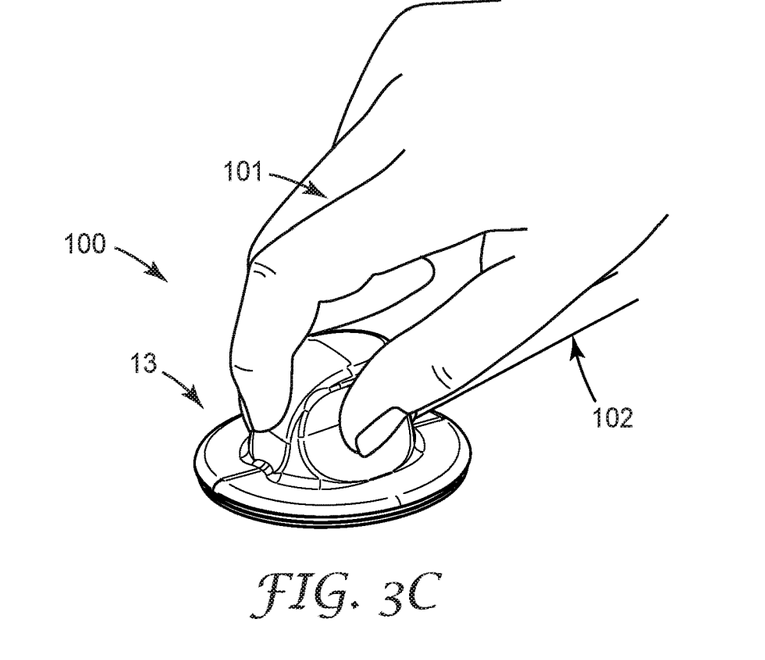

FIG. 3C illustrates where the thumb of the hand 101 contacts one of indented gripping surfaces (lateral), the index finger contacts the front indented gripping surface, and optionally, the ring finger contacts a lateral indented gripping surface.

Figure 3D:
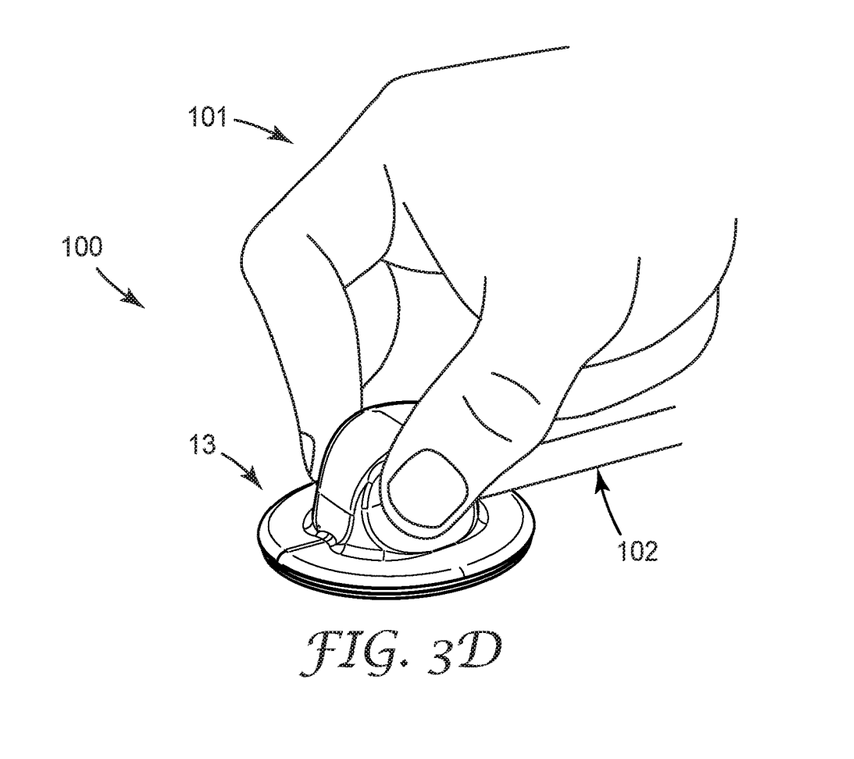

FIG. 3D illustrates where the thumb of the hand 101 contacts a first lateral indented gripping surface and the index finger contacts a second lateral indented gripping surface.

FIGS. 4A-4C illustrate an embodiment of a chestpiece 200. The chestpiece 200 can be a pediatric chestpiece 200. The chestpiece 200 can have a raised center portion 226 similar to raised center portion 26 described in FIGS. 2A-2G herein. The raised center portion 226 can have a stem portion 238 disposed thereon. The chestpiece 200 can have an outer perimeter 243. In at least one embodiment, the outer perimeter 243 can be an elliptical shape, preferably a circle. The raised center portion 226 can have a top surface 229.

The top surface 229 can be defined by an elliptical shape 216 having a major radius of curvature 219 and a minor radius of curvature 217. An aspect of the chestpiece 200 is that the ratio of radius 220 of the outer perimeter 243 to the radius of curvature (in the case of an ellipse, measured from the minor radius 217) of the top surface 229 is no greater than 2.5, no greater than 2.3, no greater than 2.1, or no greater than 2.0. The ratio of the radius 220 to the radius 217 of the chestpiece 200 can be less than that of the comparable ratio of chestpiece 13. For example, chestpiece 13 of FIG. 1 can have a ratio of between 3 and 2.4 (inclusive), or more preferably, between 2.5 and 2.7 (inclusive).

The chestpiece 200 can also have a front indented gripping surface 274 similar to indented surface 74 discussed in FIGS. 2A-2G herein. The front indented surface 274 can be arcuate to an ellipse 215. The ellipse 215 can have a major radius 213 and a minor radius 214. Dimensions of the major radius and minor radius of the ellipse can be sufficient to conform to a finger of a user. For example, the major radius can be between 5 to 15 mm (inclusive), or preferably, between 7 to 10 mm (inclusive) and the minor radius can be between 1 to 6 mm (inclusive) or preferably, between 2 mm to 4 mm (inclusive). In at least one embodiment, the ellipse 215 shape can be parallel to the bottom surface 41. In at least one embodiment, the ellipse 215 is at least one portion of an elliptical prism wherein portions of the front indented gripping surface 274 are arcuate about one or more ellipses of the elliptical prism.

The chestpiece 200 can have one or more lateral indented gripping surfaces, e.g., surface 228 which are similar to indented gripping surface 28 discussed herein. In at least one embodiment, the indented gripping surface 228 can be defined by an ellipse 201 having a major radius 203 and a minor radius 202. In at least one embodiment, the major radius 203 of such an ellipse can be oriented orthogonal to a plane formed by a bottom surface 241 and the minor radius can be oriented parallel to the plane formed by the bottom surface 241. Dimensions of the major radius and minor radius of the ellipse can be sufficient to conform to a finger of a user. For example, the major radius can be between 5 to 9 mm (inclusive), or preferably, between 6 to 8 mm (inclusive) and the minor radius can be between 1 to 5 mm (inclusive) or preferably, between 3 mm to 4 mm (inclusive).

In at least one embodiment, the chestpiece 200 can be single-patient use. For example, a method can be performed that includes contacting at least the chestpiece described herein with a patient to monitor for the auscultatory sounds. Before ever contacting the chestpiece with a second patient, the chestpiece is disposed. In at least one embodiment, disposing of the chestpiece means incineration or throwing the chestpiece in the garbage. A second chestpiece may be used with the second patient.

List of Illustrative Embodiments

1. An ergonomic chestpiece for a stethoscope adapted to receive auscultatory sounds from a patient and adapted to be coupled to an earpiece for a user, the chestpiece adapted to be grasped by two lateral sides of two fingers of the user or by a thumb and at least one finger of the user, comprising:
    a bottom surface which is generally planar adapted to be placed near the patient for receiving said auscultatory sounds;
    a raised center portion defining first and second lateral indented gripping surfaces, the raised center portion having a top surface opposite the bottom surface; and
    a stem portion extending distally from the raised center portion;
    wherein a first lateral indented gripping surface is defined by a first wall comprising a first concave surface arcuate about a first axis,
    wherein the second lateral indented gripping surface is defined by a second wall comprising a second concave surface arcuate about a second axis,
    wherein the first axis and the second axis form a V-shape comprising an apex oriented in a direction of the stem portion.
2. The ergonomic chestpiece of embodiment 1, wherein the top surface of the raised center portion is sloped with respect to said bottom surface, said top surface being closer to said bottom surface at the front of said chestpiece than at the rear of said chestpiece.
3. The ergonomic chestpiece of embodiments 1 or 2, wherein the raised center portion forms a physical stop for the two lateral sides of two fingers from contacting.
4. The ergonomic chestpiece of any of embodiments 1 to 3, wherein the bottom surface comprises a rim portion forming a diaphragm opening therein.
5. The ergonomic chestpiece of any of embodiments 1 to 4, further comprising an upper surface opposite a portion of the bottom surface.
6. The ergonomic chestpiece of embodiment 5, wherein a bell cavity is formed from the rim portion, the interior side of upper surface, and the interior side of the raised center portion.
7. The ergonomic chestpiece of any of embodiments 1 to 6, wherein the stem portion is generally parallel to the bottom surface.
8. The ergonomic chestpiece of any of embodiments 1 to 6, wherein the stem portion is askew relative to an axis parallel to the bottom surface.
9. The ergonomic chestpiece of embodiments 7 or 8, wherein the stem portion is fluidically coupled to the bell cavity.
10. The ergonomic chestpiece of any of embodiments 1 to 9, wherein the V-shape comprises an angle of between 5 and 35 degrees.
11. The ergonomic chestpiece of embodiment 10, wherein the V-shape is between 12 and 14 degrees.
12. The ergonomic chestpiece of any of embodiments 1 to 11, wherein a concave surface is continuous along an entire wall.
13. The ergonomic chestpiece of any of embodiments 1 to 12, wherein the first or second concave surface has a radius of curvature of no greater than 20 mm.
14. The ergonomic chestpiece of any of embodiments 1 to 13, wherein the first and second lateral indented gripping surfaces each comprise a protruding edge on the top surface.
15. The ergonomic chestpiece of embodiment 14, wherein a horizontal distance of the protruding edge relative to a median-most point of the first concave surface is from 1 to 4 mm (inclusive) measured along a plane parallel to a plane formed from the bottom surface.
16. The ergonomic chestpiece of embodiment 15, wherein the horizontal distance is 2.49 mm.
17. The ergonomic chestpiece of any of embodiments 1 to 16, wherein the raised center portion has a first height, wherein the first height is defined from a portion of the top surface to a portion of the bottom surface.
18. The ergonomic chestpiece of embodiment 17, wherein the first height is from 15 mm to 30 mm (inclusive).
19. The ergonomic chestpiece of embodiment 18, wherein the first height is about 21 mm.
20. The ergonomic chestpiece of any of embodiments 1 to 19, wherein the first axis and second axis are generally parallel to the bottom surface.
21. The ergonomic chestpiece of any of embodiments 1 to 20, wherein the first axis and second axis form an angle no greater than 15 degrees relative to a plane formed from the bottom surface.
22. The ergonomic chestpiece of any of embodiments 1 to 21, wherein the first and second gripping surfaces adapted to receive two lateral sides of two fingers of the user.
23. The ergonomic chestpiece of any of embodiments 1 to 22, wherein the first or second lateral indented gripping surfaces have a roughened texture.
24. The ergonomic chestpiece of embodiment 23, wherein the indented gripping surfaces have a regularly scored surface.
25. The ergonomic chestpiece of any of embodiments 1 to 24, further comprising at least one finger recess located on said top surface of said chestpiece.
26. The ergonomic chestpiece of any of embodiments 1 to 25, wherein the raised center portion further comprises a front indented gripping surface defined by a front wall.
27. The ergonomic chestpiece of embodiment 26, wherein the front wall comprises a third concave surface arcuate about a third axis.
28. The ergonomic chestpiece of embodiments 26 or 27, wherein the third axis is parallel to a plane formed by the bottom surface.
29. The ergonomic chestpiece of embodiment 28, wherein the third axis, the second axis, and the first axis form a triangle.
30. The ergonomic chestpiece of any of embodiments 26 to 29, wherein the front wall comprises a finger recess formed therein.
31. The ergonomic chestpiece of embodiment 30, wherein a finger recess is located on at least one of the indented gripping surfaces.
32. The ergonomic chestpiece any of embodiments 1 to 31, wherein the bottom surface is an elliptical shape and configured to mate with a diaphragm.
33. The ergonomic chestpiece embodiment 32, wherein the bottom surface is circular.
34. The ergonomic chestpiece of any of embodiments 1 to 33, wherein the chestpiece comprises a polymeric material.

35. The ergonomic chestpiece of any of embodiments 1 to 34, wherein the chestpiece comprises a metal.
36. The ergonomic chestpiece of any of embodiments 1 to 35, wherein a portion of the chestpiece is arcuate about a fourth axis.
37. The ergonomic chestpiece of embodiment 36, wherein a portion of the chestpiece arcuate about a fifth axis.
38. The ergonomic chestpiece of embodiment 36 or embodiment 37, wherein the fourth axis or the fifth axis are generally normal to the bottom surface.
39. The ergonomic chestpiece of any of embodiments 36 to 38, wherein a portion of the lateral indented gripping surface is arcuate about the fourth or fifth axis.
40. The ergonomic chestpiece of any of embodiments 36 to 38, wherein a portion of a protruding edge is arcuate about the fourth or fifth axis.
41. The ergonomic chestpiece of embodiment 39 or embodiment 40, wherein the portion has a radius of curvature of at least 20 mm.
42. The ergonomic chestpiece of embodiment 39 or embodiment 40, wherein the radius of curvature of the portion is at least one-fourth of a radius of curvature of an outer perimeter.
43. The ergonomic chestpiece of any of embodiments 1 to 42, wherein the chestpiece has a uniform wall thickness.
44. The ergonomic chestpiece of embodiment 43, wherein the raised center portion is hollow.
45. The ergonomic chestpiece of any of embodiments 1 to 42, wherein the raised center portion is solid with a tubular connection between the stem portion and the lower portion formed therein.
46. The ergonomic chestpiece of embodiment 45, wherein a bell cavity is formed with a hollow portion therein.
47. The ergonomic chestpiece of any of embodiments 1 to 46, wherein the first or second concave surface is also arcuate about an elliptical shape.
48. The ergonomic chestpiece of embodiment 47, wherein the elliptical shape is a circle.
49. The ergonomic chestpiece of embodiment 47, wherein the elliptical shape is an ellipse.
50. The ergonomic chestpiece of embodiment 47, wherein the elliptical shape is an elliptical prism oriented along the first or second axis.
51. The ergonomic chestpiece of embodiments 49 or 50, wherein the ellipse has a minor radius and a major radius.
52. The ergonomic chestpiece of embodiment 51, wherein the major radius is oriented orthogonal to a plane formed from the bottom surface.
53. The ergonomic chestpiece of embodiments 49 or 51, wherein the minor radius is oriented parallel to a plane formed from the bottom surface.
54. The ergonomic chestpiece of any of embodiments 51 to 53, wherein the major radius has dimensions between 5 to 9 mm (inclusive), and the minor radius has dimension between 1 to 5 mm (inclusive).
55. The ergonomic chestpiece of any of embodiments 1 to 54, wherein the ratio of a first radius of an outer perimeter of the chestpiece to a second radius of the top surface is no greater than 2.6.
56. The ergonomic chestpiece of any of embodiments 1 to 55, wherein the ratio of a first radius of an outer perimeter of the chestpiece to a second radius of the top surface is no greater than 2.
57. The ergonomic chestpiece of embodiments 55 or 56, wherein the top surface has an ellipse shape and the bottom surface has a circle shape.
58. The ergonomic chestpiece of any of embodiments 55 to 57, wherein the second radius is a minor radius.
59. The ergonomic chestpiece of any of embodiments 27 to 58, wherein the third concave surface is arcuate about an elliptical shape.
60. The ergonomic chestpiece of embodiments 59, wherein the elliptical shape is an elliptical prism oriented along the third axis.
61. The ergonomic chestpiece of embodiments 59 or 60, wherein the major radius of an ellipse of the elliptical prism is oriented parallel to a plane formed from the bottom surface.
62. The ergonomic chestpiece of any of embodiments 59 to 61, wherein the minor radius of an ellipse is oriented parallel to a plane formed from the bottom surface.
63. The ergonomic chestpiece of any of embodiments 59 to 62, wherein the major radius has dimensions between 5 to 9 mm (inclusive), and the minor radius has dimension between 1 to 5 mm (inclusive).
64. A stethoscope comprising:
    the ergonomic chestpiece of any of embodiments 1 to 63;
    a diaphragm removably attached to the ergonomic chestpiece;
    a headset; and
    tubing that couples the headset to the ergonomic chestpiece.
65. The stethoscope of embodiment 64, wherein the stethoscope is single-patient use.
66. A kit comprising:
    the ergonomic chestpiece of any of embodiments 1 to 63, and
    a diaphragm.
67. The kit of embodiment 66, further comprising:
    a headset; and
    tubing.
68. A method comprising:
    contacting a portion of the ergonomic chestpiece of any of embodiments 1 to 63 with a first patient,
    disposing of the ergonomic chestpiece without contacting the ergonomic chestpiece with a second patient.
69. The method of embodiment 68, further comprising:
    obtaining a second ergonomic chestpiece of any of embodiments 1 to 63;
    contacting a portion of the second ergonomic chestpiece with the second patient.

It shall be understood that different chestpieces differing with respect to the number, placement and form of the operational controls could be substituted for the specific embodiment shown without departing from the scope of the present invention.

What is claimed is:

1. An ergonomic chestpiece for a stethoscope adapted to receive auscultatory sounds from a patient, comprising:
    a bottom surface which is generally planar adapted to be placed near the patient for receiving auscultatory sounds;
    a raised center portion defining first and second lateral indented gripping surfaces, the raised center portion having a top surface opposite the bottom surface; and
    a stem portion extending distally from the raised center portion;
    wherein a first lateral indented gripping surface is defined by a first wall comprising a first concave surface arcuate about a first axis,
    wherein the second lateral indented gripping surface is defined by a second wall comprising a second concave surface arcuate about a second axis, wherein the first axis and the second axis form a V-shape comprising an apex oriented in a direction of the stem portion; and wherein the first and second lateral indented gripping surfaces each comprise a protruding edge on the top surface, wherein a horizontal distance of the protruding edge relative to a median-most point of the first concave surface is from 1 to 4 mm (inclusive) measured along a plane parallel to a plane formed from the bottom surface.

2. The ergonomic chestpiece of claim 1, wherein the stem portion is generally parallel to the bottom surface.

3. The ergonomic chestpiece of claim 1, wherein the V-shape comprises an angle of between 5 and 35 degrees.

4. The ergonomic chestpiece of claim 3, wherein the V-shape is between 12 and 14 degrees.

5. The ergonomic chestpiece of claim 1, wherein the first or second concave surface is continuous along an entire wall.

6. The ergonomic chestpiece of claim 1, wherein the first or second concave surface has a radius of curvature of no greater than 20 mm.

7. The ergonomic chestpiece of claim 1, wherein the raised center portion further comprises a front indented gripping surface defined by a front wall, wherein a portion of the front wall comprises a third concave surface arcuate about a third axis, wherein the third axis is parallel to a plane formed by the bottom surface.

8. The ergonomic chestpiece of claim 7, wherein the third axis, the second axis, and the first axis form a triangle.

9. The ergonomic chestpiece of claim 1, wherein the chestpiece comprises a polymeric material.

10. The ergonomic chestpiece of claim 9, wherein a radius of curvature of the first or second lateral indented gripping portion is at least one-fourth of a radius of curvature of an outer perimeter.

11. The ergonomic chestpiece of claim 1, wherein the first concave surface is also arcuate about an elliptical shape.

12. The ergonomic chestpiece of claim 11, wherein the elliptical shape is an elliptical prism oriented along the first axis.

13. The ergonomic chestpiece of claim 12, wherein the elliptical prism comprises an ellipse, wherein the ellipse has a minor radius and a major radius, wherein the major radius has dimensions between 5 to 9 mm (inclusive), and the minor radius has dimension between 1 to 5 mm (inclusive).

14. The ergonomic chestpiece of claim 1, wherein the top surface is an ellipse and the outer perimeter is circular.

15. The ergonomic chestpiece of claim 14, wherein a ratio of a first radius of the outer perimeter of the chestpiece to a second radius of the top surface is at least 1:9, wherein the second radius is a minor radius.

16. The ergonomic chestpiece of claim 7, wherein the third concave surface is arcuate about an elliptical prism oriented along the third axis.

17. The ergonomic chestpiece of claim 16, wherein the elliptical prism comprises an ellipse and the major radius has dimensions between 5 to 9 mm (inclusive), and the minor radius has dimension between 1 to 5 mm (inclusive).

18. A stethoscope comprising:
the ergonomic chestpiece of claim 1;
a diaphragm removably attached to the ergonomic chestpiece;
a headset; and
tubing that couples the headset to the ergonomic chestpiece.

19. A method comprising:
contacting a portion of the ergonomic chestpiece of claim 1 with a first patient, and
disposing of the ergonomic chestpiece without contacting the ergonomic chestpiece to a second patient.

* * * * *